United States Patent [19]

Ogata et al.

[11] Patent Number: 4,870,071
[45] Date of Patent: Sep. 26, 1989

[54] PROPHYLACTIC AND THERAPEUTIC AGNET FOR HEPATIC DISORDER

[75] Inventors: Kazumi Ogata, Toyonaka; Takahiro Sakaue, Itami, both of Japan

[73] Assignee: Senju Pharmaceutical Co., Ltd., Osaka, Japan

[21] Appl. No.: 44,890

[22] Filed: Apr. 30, 1987

[30] Foreign Application Priority Data

May 1, 1986 [JP] Japan ................................ 61-101755

[51] Int. Cl.$^4$ .................... A61K 31/33; A61K 31/425
[52] U.S. Cl. .................................... 514/191; 514/365; 514/562; 514/893; 514/894
[58] Field of Search ............... 514/191, 365, 562, 893, 514/894

[56] References Cited

FOREIGN PATENT DOCUMENTS 37-16735 10/1962 Japan .
56-150075 11/1981 Japan .
56-166189 12/1981 Japan .
57-175197 10/1982 Japan .

OTHER PUBLICATIONS

*Chemical Abstracts*, vol. 96 (1982) 143263f.

*Primary Examiner*—Frederick E. Waddell
*Attorney, Agent, or Firm*—Burgess, Ryan & Wayne

[57] ABSTRACT

There is provided the use of cysteineglucuronic acid, cysteineglucuronolactone and their salts as a prophylactic and therapeutic agent for hepatic disorder. By administering the compound to a subject in an oral dail does of 1 to 5,000 mg or parenteral daily dose of 1, to 2,000 mg, the elevation of GOT, GPT, LDH, ALP TG or HyP level is suppressed and hepatic disorders can be prevented or cured.

2 Claims, 2 Drawing Sheets

PLASMA CYSTEINE CONCENTRATION (●—●) AND CGCA CONCENTRATION (○—○) AFTER ADMINISTRATION OF CGCA. PLASMA CYSTEINE CONCENTRATION AFTER ADMINISTRATION OF CYSTEINE (▲—▲).

PROPHYLACTIC AND THERAPEUTIC AGNET FOR HEPATIC DISORDER

FIELD OF THE INVENTION

The present invention relates to a prophylactic and therapeutic agent for hepatic disorder.

BACKGROUND OF THE INVENTION

Cysteineglucuronolactone and salts thereof are described in Laid-Open Japanese Patent Application Kokai Nos. 56-166189 and 57-175197, respectively, but as regards their effects, only the effect of cysteine and that of glucuronolactone are anticipated.

There has also been disclosed a method for producing cysteineglucuronic acid or sodium cysteineglucuronate which comprises reacting cysteine with glucuronic acid or sodium gluconate but as to the application of such compounds it has been merely described that they are expected to be of use as, for example, hapatotonics and therapeutic agents for radiation disorder (Japanese Patent Publication No. 37-16735).

Further, as a compound having the actions of cysteine, glucuronic acid and calcium in one compound and having the instability of cysteine overcome, calcium cysteineglucuronate as well as a method for production thereof has been disclosed but no reference has been made to its uses except those mentioned hereinabove (Laid-Open Japanese Patent Application Kokai No. 56-150075).

An anticataract drug comprising a salt of cysteineglucuronic acid has also been disclosed (Laid-Open Japanese Patent Application Kokai No. 57-18615).

As has been mentioned just above, Japanese Patent Publication No. 37-16735 does not disclose any information on the application of cysteineglucuronic acid other than the possible uses referred to above. Any use invention in the pharmaceutical field comes to be established only after its relevant utility has been sufficiently demonstrated and verified by a series of biological experiments and tests and the description in the above-mentioned patent literature cannot be said to teach pharmaceutical uses in the genuine sense of the term.

Therefore, one must conclude that the effects of cysteineglucuronolactone, cysteineglucuronic acid and their respective salts on the liver, for example, the effects of such compounds on acute or chronic hepatitis and hepatocirrhosis, have not been elucidated as yet.

The present invention has resolved the question and provides new uses for the above-mentioned compounds.

SUMMARY OF THE INVENTION

The research undertaken by the present inventors into the pharmacology of cysteineglucuronolactone and cysteineglucuronic acid and their salts showed that these substances on oral administration are translocated into the bloodstream where they are respectively decomposed to cysteine and glucuronic acid and that these substances exert overt inhibitory activity against onset of various liver disorders.

Predicated on the above new findings, the present invention is directed to the following aspects:

A prophylactic and therapeutic agent for hepatic disorder which comprises cysteineglucuronic acid, cysteineglucuronolactone or a pharmaceutically acceptable salt of either compound;

A prophylactic and therapeutic composition for hepatic disorder which comprises an effective amount of the compound or the salt and a carrier;

A dosage unit of the compound or the salt for use in preventing or curing hepatic disorder which comprises one to less than one preferably one to one fourth, amount of daily dose of the compound or the salt, wherein the daily dose is 1 to 5,000 mg, preferably 10 to 2,000 mg for oral administration and 1 to 2,000 mg, preferably 10 to 1,000 mg for parenteral administration;

A process for preventing from or combatting with hepatic disorder which comprises administering orally or parenterally an effective daily dose of the compound or the salt to a subject; and A process for suppressing the elevation of the GOT, GPT, LDT or ALP level in blood, or the TG or HyP level in liver which comprises administering orally or parenterally an effective daily dose of the compound or the salt to a subject.

DETAILED DESCRIPTION OF THE INVENTION

Cysteineglucuronic acid is a condensation product of cysteine and glucuronic acid, which can be obtained by reacting the two starting compounds in aqueous medium within the range of pH 4 to pH 10 and, as such, contains two carboxyl groups originated from cysteine and glucuronic acid, respectively, although depending on conditions of the above reaction, it is usually obtained as a reaction product with one of said two carboxyl groups having been neutralized in the form of a salt as shown in the formula:

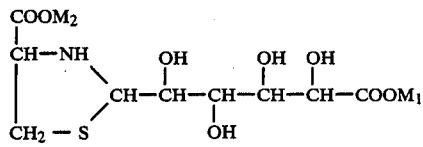

wherein $COOM_1$ represents a carboxyl group converted to a salt and $COOM_2$ represents a carboxyl group or a carboxyl group converted to a salt.

When the above condensation reaction is carried out while adjusting the pH of the reaction mixture with the hydroxide or carbonate of sodium, potassium, calcium or magnesium, for instance, cysteineglucuronic acid is obtained in the form of the corresponding salt.

Cysteineglucuronolactone of the formula given below can be obtained by reacting cysteine with glucuronolactone in water.

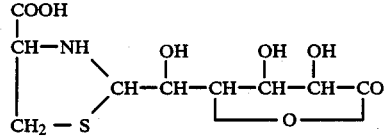

Neutralization of the above product with the hydroxide or carbonate of sodium or potassium, for instance, gives the corresponding salt.

These salts should be preferably be pharmaceutically acceptable ones, for example sodium, potassium, calcium, magnesium and aluminum salts.

The agent according to this invention can inhibit the onset of acute and chronic liver disorders and thus suppresses increase in GOT, GPT and hydroxyproline levels. Furthermore, it can inhibit the progress of hepatic fibrosis as found, for example, in liver cirrhosis and still further can suppress an increase in liver TG level due to intake of alcoholic drinks.

The agent according to this invention can be administered either orally or parenterally.

For oral administration, cysteineglucuronolactone and cysteineglucuronic acid, each preferably in the form of a salt such as the calcium or magnesium salt, can be administered in such dosage form as tablets, pills, capsules, granules and solutions.

For parenteral administration, cysteineglucuronic acid salts, preferably in the form of an aqueous solution of a water-soluble salt such as the sodium or potassium salt, can be administered subcutaneously, intramuscularly or intravenously, for example.

The above-mentioned dosage forms can generally be prepared in the form of a composition by blending the compound according to this invention with a suitable carrier in the conventional manner.

For example, the compound according to this invention is admixed with an excipient such as starch or lactose and a lubricant such as magnesium stearate or talc and the mixture is tableted to give tablets for oral administration.

It is also possible to obtain injectable solutions by dissolving the compound in the form of sodium or potassium salt in distilled water to serve as the agent or the composition according to this invention, adjusting the pH of the solution to that of body fluids with the hydroxide or carbonate of sodium or potassium if necessary, further adding an isotonizing agent and then filtering the solution for the removal of microorganisms.

The agent or composition for hepatic disorder according to this invention can contain other pharmaceutically active ingredients than the compounds mentioned above unless said ingredients are unfit for the purpose of the invention.

Cysteineglucuronic acid and salts thereof, which serve as the liver disorder antagonizing ingredients according to the invention, are substantially nontoxic, as indicated by the results of acute toxicity testing in mice, which are shown below.

| Acute toxicity of the compounds according to the invention in terms of $LD_{50}$ (intravenous injection) | | | |
|---|---|---|---|
| No. | Kind* | | $LD_{50}$ |
| 1 | Monosodium salt | Male and female | 2.5 g/kg |
| 2 | Dipotassium salt | Male | 250 mg/kg |
| 3 | Calcium salt | Male | 100 mg/kg |
|  |  | Female | 200 mg/kg |
| 4 | Magnesium salt | Male | 250 mg/kg |

*The kind of the cysteineglucuronic acid salt is indicated.

Referring to the above table, the injection No. 1 was adjusted to pH 7.0–7.2 by adding sodium carbonate after dissolution of the sample. The injection No. 3 showed somewhat increased toxicity presumably due to physical factors associated with the low solubility of the calcium salt.

In an acute oral toxicity test in mice, cysteine-glucuronic acid monosodium salt gave an $LD_{50}$ value of 7.5 g/kg and also the corresponding calcium salt gave an $LD_{50}$ value of 7.5 g/kg.

The dose of the compound to be used according to the invention may vary depending on the symptom and the route of administration. For oral administration, the compound can be administered generally in a daily dose of 1 to 5,000 mg, preferably in a daily dose of 10 to 2,000 mg, per human adult and, for injection, in a daily dose of 1 to 2,000 mg, preferably 10 to 1,000 mg. Such daily dose may be administered in one to several divided doses.

In the following examples, typical pharmacological properties of the compounds to be utilized according to the invention are illustrated by test results in rabbits and rats. It has been widely recognized in the art that these animals are trustworthy models of humans with respect to the relevant pharmacological activities.

EXAMPLE 1

Transfer to plasma and plasma level duration transfer to plasma of cysteineglucuronic acid calcium salt (CGCa) after oral administration and the plasma level duration were investigated in rabbits.

<Test method>

CGC was orally administered to rabbits in a dose of 500 mg/kg and after 0, 2, 4, 6, . . . and 24 hours, the blood was sampled. The sera separated from the blood samples were deproteinized with trichloroacetic acid and, then, free cysteine in the sera as well as cysteine resulting from hydrolysis following heating was determined by fluorescence labeling and high performance liquid chromatography (HPLC).

<Test results>

Figure 1:
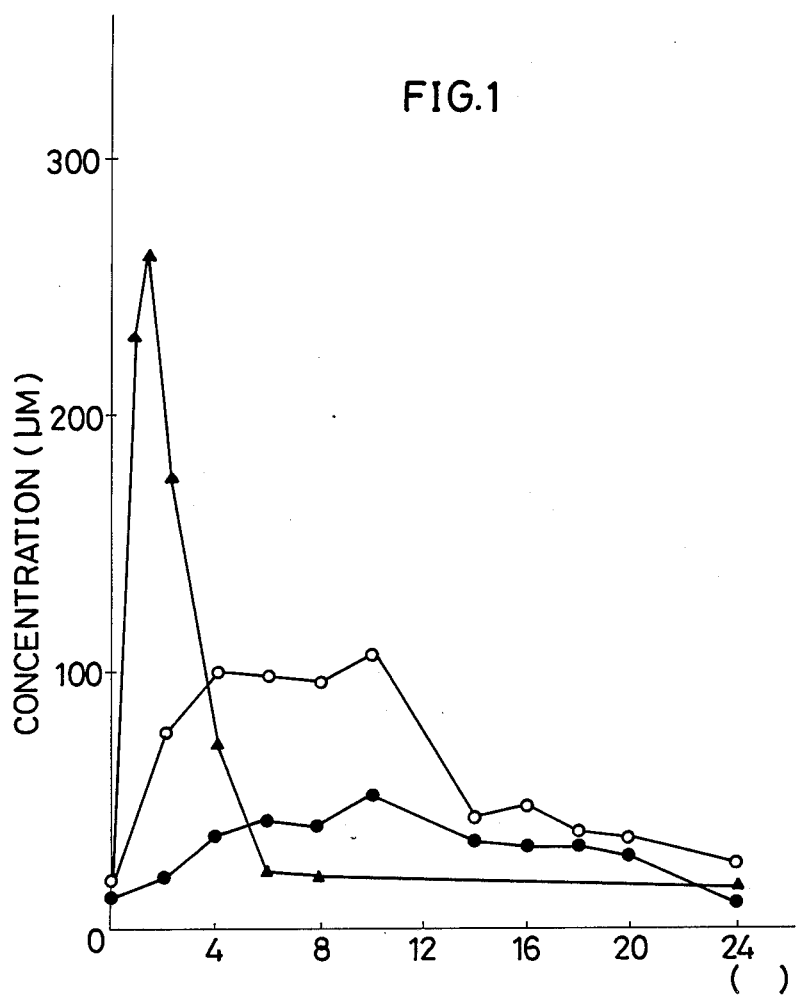
FIG. 1 is a blood concentration-time curve of CGCa (c cysteineglucuronate) in the experiment described in Example 1. graphs showing the histological picture of hepatocytes (stained with hematoxilineosin, ×10) in CCl4-induced chronic liver disorder experiment described in Example 2 (B)

As shown in FIG. 1, the free cysteine content in plasma began to increase gradually after the lapse of 2 hours following oral administration of CGCa and a maximum value of 50 μM was maintained during the period of hours 6–10. After 24 hours, said content was at a normal value ( ●—● ). On the other hand, the curve described by (○—○) the total content of cysteine after hydrolysis. Hence, the difference between the (○—○) and the ( ●—●) value corresponds to the content of that portion of cysteine which was formed by hydrolysis.

Since, before CGCa administration, the cysteine content after hydrolysis did not show any substantial increase, that portion of cysteine which formed upon hydrolysis after CGCa administration may be considered to have been derived from CGCa. Therefore, the CGCa content is in correlation with the cysteine content and thus the cysteine content was maintained at increased levels while CGCa was present in the plasma. Since the administration of CGCa results in gradual conversion to cysteine, it can be concluded that increased blood cysteine levels can be maintained for a prolonged period as compared with the administration of an equimolar amount of cysteine ( ▲—▲ ).

EXAMPLE 2

Effect on carbon tetrachloride-induced hepatic disorder

Carbon tetrachloride (CCl$_4$) is in wide use in studies of experimental hepatic disorder. The disorder is considered to be caused by lipid peroxides resulting from covalent bonding of CCl$_3$ to lipids in the liver microsome.

(A)-1

Effect on CCl$_4$-induced acute hepatic disorder

<Test method>

Wistar-strain male rats were used after fasting. Six groups were used: (1) control group, (2) CGCa I group (CGCa administration 12 hours before CCl$_4$ administration), (3) CGCa II group (CGCa administration 10 hours before CCl$_4$), (4) CGCa III group (CGCa administration 8 hours before CCl$_4$), (5) CGCa IV group (CGCa administration 6 hours before CCl$_4$), and (6) CGCa V group (CGCa administration 4 hours before CCl$_4$).

In the control group, 0.5% carboxymethylcellulose was orally administered in a dose of 20 ml/kg and, in the CGCa I-V groups, CGCa was orally administered in a dose of 2.0 g/20 ml (0.5% CMC)/kg. The hepatic disorder inducer CCl$_4$ was intraperitoneally administered to each group in a dose of 0.08 ml/kg (diluted with olive oil so as to give a dose volume of 5 ml/kg) and, after about 18 hours, the blood was sampled for the assay of s-GOT and s-GPT. The test schedule was as given in the following table.

TABLE 1

| Group | s-GOT | s-GPT | n. |
|---|---|---|---|
| Control | 1662.1 ± 643.54 | 494.8 ± 187.07 | 7 |
| CGCa I group | 1134.9 ± 361.57 | 310.5 ± 68.08* | 8 |
| CGCa II group | 921.6 ± 198.34* | 308.5 ± 42.30* | 7 |
| CGCa III group | 929.0 ± 201.14* | 328.2 ± 105.72 | 7 |
| CGCa IV group | 1493.3 ± 480.60 | 502.4 ± 210.66 | 8 |
| CGCa V group | 1453.0 ± 515.58 | 516.3 ± 166.50 | 8 |

(in Karmen units)
Significance of difference relative to the control group:
*p < 0.05;
 0.05 < p < 0.10

When CGCa was administered 8 to 10 hours earlier than CCl$_4$, the CCl$_4$-induced increase of s-GOT was significantly suppressed (p<0.05), whereas the increase of s-GPT was significantly suppressed by 10 or 12 hours earlier administration of CGCa (p<0.05).

(A)-2

Effect on CCl$_4$-induced acute hepatic disorder

Male Wistar rats were used after fasting in four groups: (1) control group, (2) CGCa I group, (3) CGCa II group and (4) CGCa III group. In the control group, 0.5% CMC was orally administered in a dose of 20 ml/kg and, in the CGCa I, II and III groups, CGCa was orally administered in doses of 1.02, 1.43 and 2.0 g/20 ml (0.5% CMC)/kg (common ratio 1.4), respectively. Ten hours later, CCl$_4$ was intraperitoneally administered in a dose of 0.08 ml/kg. About 18 hours thereafter, the blood was sampled for the assay of s-GOT and s-GPT.

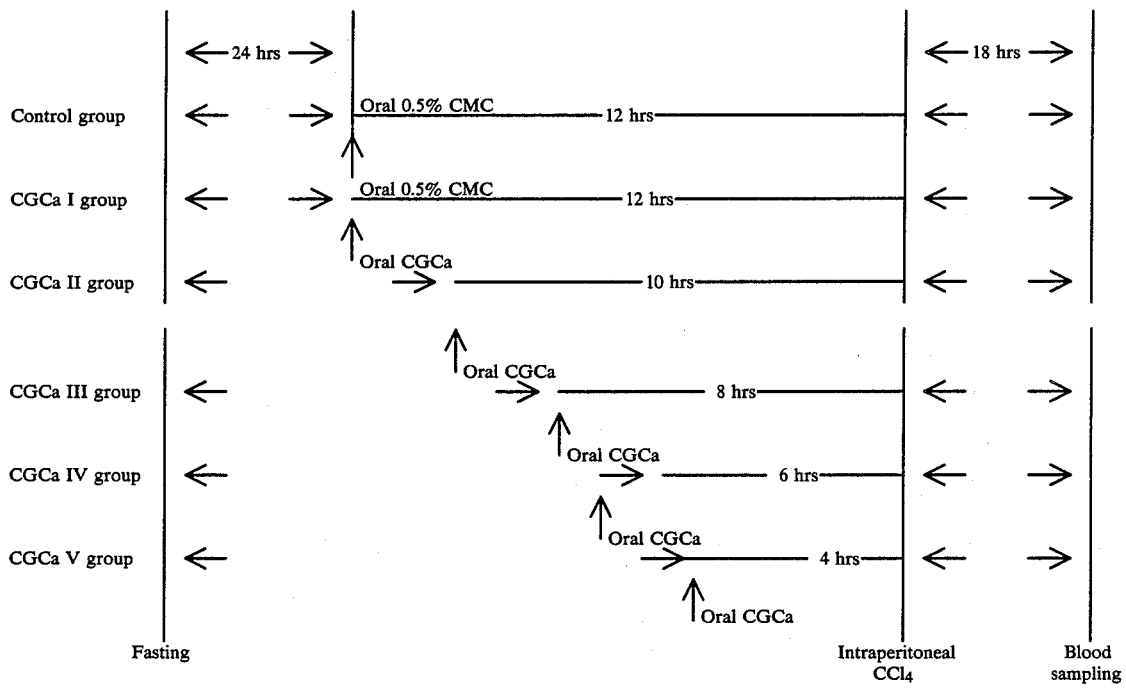

<Test results>

The s-GOT and s-GPT values obtained are shown in Table 2.

Administration of 1.43 g/kg of CGCa significantly suppressed the increase of s-GPT (p<0.05) and caused <Test Results>

The s-GOT and s-GPT values obtained are shown in Table 1.

a tendency toward suppression of the increase in s-GOP. At 2.0 g/kg, the increases in s-GOP and s-GPT were significantly suppressed (p<0.05).

TABLE 2

| Group | s-GOT and s-GPT values | | n. |
|---|---|---|---|
| | s-GOT | s-GPT | |
| Control group | 1844.9 ± 899.87 | 539.2 ± 264.99 | 9 |
| CGCa I group | 1755.6 ± 784.49 | 427.2 ± 131.72 | 8 |
| CGCa II group | 1192.0 ± 264.07 | 309.5 ± 86.25* | 8 |
| CGCa III group | 1106.2 ± 224.53* | 299.9 ± 79.85* | 8 |

(in Karmen units)
Significance of difference relative to the control group:
**p < 0.01;
*p < 0.05;
 0.05 < p < 0.10.

(B)

Effect on CCl₄-induced chronic hepatic disorder

<Test method>

Male SD rats were used in two groups, namely the control group and the CGCa group.

In the control group, a powder diet (Clea Japan's CE-2) was given to the animals and, in the CGCa group, the animals were given a mixture of said powder diet and 5% of CGCa.

$CCl_4$ was dissolved in olive oil in a concentration of 10% (w/v) and the solution was intraperitoneally administered in a dose of 5 ml/kg twice a week (Tuesday and Friday) for 10 weeks. Three days after the last $CCl_4$ administration, blood samples were collected in each group for the assay of s-GOT, s-GPT, etc. Assay of liver hydroxyproline (HyP) and pathological examination of the liver following H.E. staining were also performed.

<Test results> biochemistry data and HyP values obtained for the control and CGCa groups are shown in Table 3.

TABLE 3

| Parameter | Data by biochemical determination | | |
|---|---|---|---|
| | (unit) | Control group | Group CGCa |
| s-GOT | (Karmen units) | 742.9 ± 451.15 | 358.9 ± 157.13* |
| s-GPT | (Karmen units) | 257.0 ± 142.13 | 130.3 ± 53.56* |
| LDH | (Wroblewski units) | 944.1 ± 496.95 | 491.7 ± 312.24# |
| ALP | (King-Armstrong units) | 44.6 ± 15.56 | 59.5 ± 23.83 |
| Total bilirubin | (mg/dl) | 0.31 ± 0.033 | 0.35 ± 0.108 |
| γ-GTP | (mU/ml) | 3.9 ± 4.45 | 3.0 ± 1.50 |
| Cholinesterase | (ΔpH) | 0.018 ± 6.67 × 10⁻³ | 0.014 ± 5.16 × 10⁻³ |
| Albumin | (g/dl) | 3.3 ± 0.20 | 3.4 ± 0.28 |
| Serum iron | (μg/dl) | 243.8 ± 57.73 | 215.0 ± 39.01 |
| Liver HyP | (μg/g) | 583.9 ± 182.81 | 371.6 ± 93.05* |
| n. | | 9 | 10 |

Significance of difference from the control group: *p < 0.05; #0.05 < p < 0.10

CGCa significantly suppressed elevations of s-GOT and s-GPT (p<0.05) and tended to suppress an elevation of LDH (0.05<p<0.10).

In addition, CGCa significantly suppressed an elevation of Hyp (p<0.05).

Figure 2A:
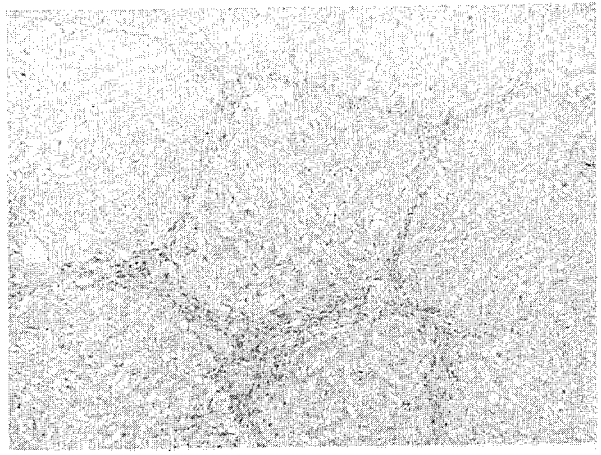
FIG. 2 (A) represents the control group and FIG. 2 (B) represents the CGCa treatment group.
Figure 2B:
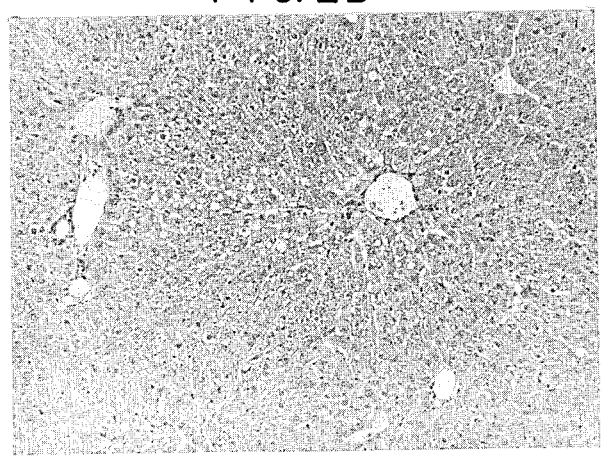

Pathologically, the control group showed a picture of hepatocirrhosis, characterized by marked necrosis of hepatocytes and formation of pseudolobules. Cellular infiltration mainly of lymphocytes was prominent and vacuoles suggesting a fatty change were found. On the other hand, in the CGCa group, although vacuolar degeneration was found, the original lobular structure of the liver was preserved without evidence of hepatocirrhosis, such as formation of pseudolobules. Necrosis was scattered and cellular infiltration was slight as compared with the control group (FIG. 2).

The above results suggest that CGCa suppresses an increase in HyP, which is an indicator of escaping enzymes and hepatic fibrosis, both reflecting inflammation, necrosis and degeneration of hepatocytes, and histopathological evalution showed that CGCa is effective against the damage and fibrosis of hepatocytes.

In further experiments in which cysteineglucuronolactone (CGL) and sodium cysteineglucuronate (CGNa) were respectively administered orally in a dose of 2.0 g/kg 1 hour earlier than intraperitoneal administration of 0.08 ml/kg of $CCl_4$, the percent suppressions of s-GOT and s-GPT obtained as compared with the control group were as shown below.

| | Suppression of s-GOT | Suppression of s-GPT |
|---|---|---|
| CGL | 35.0% | 34.8% |
| CGNa | 37.2% | 39.3% |

EXAMPLE 3

Effect on acetaminophen-induced hepatic disorder

Acetaminophen, while it is a good antipyretic analgesic, causes severe liver damage when administered in large doses. It is said that this is due to liver cell necrosis caused by the covalent bonding to liver proteins of the harmful intermediate metabolite aryl compound, forming as a result of an acetaminophen dose-related decrease in liver glutathione level, hence a decrease in the capacity to detoxify acetaminophen by conjugation.

In this experiment, cysteineglucuronolactone and cysteineglucuronic acid salts (CG groups) were tested for their effects on acetaminophen-induced hepatic disorder in terms of their ability to suppress elevations in serum GOT, GPT, LDH and ALP.

<Test method>

Male SD rats were used after 24 hours of fasting. In the control and normal groups, 10 ml/kg of 0.5% CMC was orally administered and, in the CG groups, 500 mg/10 ml/kg of the respective compound was orally administered. An hour later, 400 mg/15 ml/kg of acetaminophen was intraperitoneally administered to the control and CG groups while 15 ml/kg of physiological saline was intraperitoneally administered to the normal group. After 24 hours, the rats were sacrificed and the sera were separated and assayed for GOT, GPT, LDH and ALP.

‹Test results›

The results of assay of serum GOT, GPT, LDH and ALP for each group are shown in Table 4.

In the CG groups, significant suppression of the acetaminophen-induced hepatic disorder was attained.

TABLE 4

| Group | s-GOT | s-GPT | LDH | ALP |
|---|---|---|---|---|
| Control | 1065.0 ± 297.7 | 348.4 ± 131.6 | 2973.4 ± 1213.3 | 14.5 ± 18.6 |
| CGCa GROUP | 284.2 ± 136.3*** | 121.7 ± 33.7** | 705.1 ± 283.3** | 11.4 ± 1.52** |
| CGNa group | 180.1 ± 63.0*** | 78.4 ± 13.7*** | 557.2 ± 240.7*** | 10.4 ± 1.22*** |
| CGMg group | 386.3 ± 88.1*** | 141.9 ± 27.5** | 857.5 ± 296.1** | 12.8 ± 1.20* |
| CGL group | 185.0 ± 83.3*** | 85.5 ± 22.7*** | 540.3 ± 238.1*** | 10.7 ± 1.04*** |
| Normal group | 62.0 ± 5.37*** | 26.1 ± 1.35*** | 388.0 ± 141.7*** | 11.5 ± 2.26** |

Significance of difference from the control group:
***$p < 0.001$
**$p < 0.01$
*$p < 0.05$
CGL: Cysteineglucuronolactone.
CGMg: Magnesium cysteineglucuronate.
CGNa: Sodium cysteineglucuronate.
CGCa: Calcium cysteineglucuronate.
GOT, GPT - In Karmen units.
LDH - In Wroblewski units.
ALP - In BL (Bessey-Lowry) units.
n. = 6–8

EXAMPLE 4

Effect on galactosamine-induced hepatopathy

Galactosamine-induced hepatopathy is caused by inhibition of glycoprotein and protein metabolisms and has been used as an experimental model since it pathologically resembles viral hepatitis. Therefore, the effect of CGCa on galactosamine-induced hepatopathy was investigated using s-GOT and s-GPT as indicators.

‹Test method›

Male Wistar rats were used after fasting. Three groups i.e. (1) normal group, (2) control group and (3) CGCa group, were provided.

Twenty milliliters (20 ml) per kg of 0.5% CMC was orally administered to the normal and control groups and 2.0 g/20 ml/kg of CGCa was orally administered to the CGCa group. Fifteen (15) hours later, a second administration was performed in the same dose. After a further 5 hours, 400 mg/4 ml physiological saline/kg of galactosamine hydrochloride was intraperitoneally administered to the control and CGCa groups. Twenty-four (24) hours thereafter, blood samples were collected for the assay of s-GOT and s-GPT.

‹Test results›

The s-GOT and s-GPT values thus obtained are shown in Table 5.

TABLE 5

| Group | s-GOT | s-GPT | n |
|---|---|---|---|
| Control | 2938.2 ± 1588.77 | 1174.8 ± 565.24 | 10 |
| CGCa group | 1643.1 ± 480.43* | 702.3 ± 223.08* | 9 |

(In Karmen units)
Significance of difference from the control group:
*$p < 0.05$ Administration of galactosamine hydrochloride resulted in elevations of s-GOT and s-GPT and oral administration o CGCa inhibited the elevations significantly ($p < 0.05$). Therefore CGCa can be considered to be e against galactosamine-induced hepatic disorder.

EXAMPLE 5

Effect on alcohol-induced hepatopathy

Alcohol is metabolized in vivo to give acetaldehyde, which displays toxicity. When a SH group-containing compound is present, however, acetaldehyde instantaneously combines with said compound to form a thiazoline and is thereby detoxified.

In this experiment, therefore, alcohol was forcedly given to rats by the oral route and whether CGCa was effective in inhibiting the resultant alcohol-induced hepatic disorder was examined.

‹Test Method›

Male Wistar rats were used after fasting. Three groups, (1) control group (2) CGCa group and (3) normal group, were provided.

The control and normal groups orally received 20 ml/kg of 0.5% CMC and the CGCa group orally received 2.0 g/20 ml/kg of CGCa. After 13 hours, 20% alcohol was orally administered at 5 g/kg. After 8 hours, the liver was removed and TG was determined by the acetylacetone method.

‹Test results›

The liver TG levels thus found are shown in Table 6.

TABLE 6

| Group | Liver TG | n |
|---|---|---|
| Control | 7.8 ± 1.93 | 10 |
| CGCa group | 4.4 ± 1.29* | 9 |
| Normal group | 3.4 ± 0.54** | 3 |

(In terms of mg/g liver)
Significance of difference from the control group:
**$p < 0.01$
*$p < 0.05$ Administration of alcohol significantly increased the liver TG level as compared with the normal group ($p < 0.01$). In contrast, administration of CGCa significantly suppressed this increase ($p < 0.05$).

| Dosage Form Example 1 | Tablets |
|---|---|
| Calcium cysteineglucuronate | 200 mg |
| Crystalline cellulose | 110 mg |
| Hydroxypropylcellulose | 16 mg |

-continued

| Dosage Form Example 1 | Tablets |
|---|---|
| Magnesium stearate | 4 mg |

Tablets are formed in the conventional manner using the above ingredients as the materials for one tablet. They may be film-coated or sugar-coated as necessary.

| Dosage Form Example 2 | Granules |
|---|---|
| Cysteineglucuronolactone | 50 mg |
| Lactose | 100 mg |
| Starch | 97 mg |
| Gelatin | 3 mg |

Granules are prepared by using the above ingredients in the above proportions such that the above quantities give one packet.

| Dosage Form Example 3 | Capsules |
|---|---|
| Magnesium cysteineglucuronate | 100 mg |
| Lactose | 50 mg |
| Crystalline cellulose | 95 mg |
| Talc | 5 mg |

Capsules are filled with a mixture of the above ingredients used in the above proportions such that the above quantities give one filled capsule.

Dosage Form Example 4

Injections

Monosodium cysteineglucuronate is distributed in 50-mg portions into vials for injectable solution under sterile conditions.

Separately, a solvent for injection is prepared in the conventional manner using the following:

| Disodium monohydrogen phosphate | 1.0 g |
|---|---|
| Sodium chloride | 0.8 g |
| Distilled water for injection | To make 100 ml. |

The solution is distributed in 5-ml portions into ampules, which are then sealed.

In accordance with the present invention, cysteineglucuronic acid or cysteineglucuronolactone administered orally is translocated into the bloodstream to cause significant depressions of GOT and GPT in hepatic disorder models.

In carbon tetrachloride-induced hepatic disorder, too, whereas the histopathological picture of the liver in the control group shows progression of liver fibrosis, the picture in the $CGC_2$ group shows a suppression of the fibrosis.

In biochemical examination, too, the present invention significantly inhibits an elevation of hydroxyproline which is an indicator of liver fibrosis and significantly inhibits the elevation of liver TG due to alcohol loading.

We claim:

1. A process for suppressing the elevation of GOT, GPT, LDH or ALP level in blood, or TG or HyP level in liver, of a subject suffering from hepatic disorders, which comprises administering orally or parenterally to said subject an effective daily dose for suppressing said elevation of a pharmaceutical composition comprised of a therapeutically effective amount of a compound selected from the group consisting of cysteineglucuronic acid, cysteineglucuronolactone and pharmaceutically acceptable salts thereof, and a pharmaceutically acceptable carrier.

2. The process as claimed in claim 1, wherein the effective daily dose is 1 to 5000 mg for oral administration and 1 to 2000 mg for parenteral administration.

* * * * *